US007183081B2

(12) United States Patent  
Li et al.

(10) Patent No.: US 7,183,081 B2
(45) Date of Patent: Feb. 27, 2007

(54) HUMAN CKβ-10 POLYNUCLEOTIDES

(75) Inventors: Haodong Li, Gaithersburg, MD (US); Mark D. Adams, Rockville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 10/893,995

(22) Filed: Jul. 20, 2004

(65) Prior Publication Data
US 2004/0265974 A1 Dec. 30, 2004

Related U.S. Application Data

(60) Division of application No. 10/164,621, filed on Jun. 10, 2002, now Pat. No. 6,921,645, which is a division of application No. 09/261,201, filed on Mar. 3, 1999, now Pat. No. 6,458,349, which is a division of application No. 08/458,355, filed on Jun. 2, 1995, now Pat. No. 5,981,230, which is a continuation-in-part of application No. PCT/US94/09484, filed on Aug. 23, 1994.

(51) Int. Cl.
*C12P 21/06* (2006.01)

(52) U.S. Cl. .................. 435/69.1; 435/6; 435/7.1; 536/23.1; 530/350; 530/300; 514/2; 514/12

(58) Field of Classification Search ............... 536/23.1; 435/6, 69.1, 7.1; 530/350, 300; 514/2, 12
See application file for complete search history.

(56) References Cited

U.S. PATENT DOCUMENTS

| | | | |
|---|---|---|---|
| 4,897,348 A | 1/1990 | Johnson et al. |
| 5,011,912 A | 4/1991 | Hopp et al. |
| 5,278,287 A | 1/1994 | Rollins et al. |
| 5,306,709 A | 4/1994 | Gewirtz |
| 5,346,686 A | 9/1994 | Lyle et al. |
| 5,413,778 A | 5/1995 | Kunkel et al. |
| 5,474,983 A | 12/1995 | Kuna et al. |
| 5,602,008 A | 2/1997 | Wilde et al. |
| 5,936,068 A | 8/1999 | Wilde et al. |
| 6,096,300 A | 8/2000 | Hromas |
| 6,174,995 B1 | 1/2001 | Li et al. |

FOREIGN PATENT DOCUMENTS

| | | |
|---|---|---|
| EP | 0538 030 2 | 4/1993 |
| JP | 07-089866 | 4/1995 |
| WO | WO-90/06321 | 6/1990 |
| WO | WO-91/04274 | 4/1991 |
| WO | WO-91/12815 | 9/1991 |
| WO | WO-92/05198 | 4/1992 |
| WO | WO-92/20372 | 11/1992 |
| WO | WO-95/17092 | 6/1995 |
| WO | WO-95/31467 | 11/1995 |
| WO | WO-95/31468 | 11/1995 |
| WO | WO-96/05856 | 2/1996 |
| WO | WO-96/06169 | 2/1996 |
| WO | WO-96/09062 | 3/1996 |
| WO | WO-96/16979 | 6/1996 |
| WO | WO-96/39520 | 12/1996 |
| WO | WO-96/39521 | 12/1996 |
| WO | WO-96/39522 | 12/1996 |
| WO | WO-97/31098 | 3/1997 |
| WO | WO-97/15594 | 5/1997 |
| WO | WO-97/15595 | 5/1997 |
| WO | WO-97/35982 | 10/1997 |
| WO | WO-98/01557 | 1/1998 |
| WO | WO-98/09171 | 3/1998 |
| WO | WO-98/11226 | 3/1998 |
| WO | WO-98/14573 | 4/1998 |
| WO | WO-98/17800 | 4/1998 |
| WO | WO-98/21330 | 5/1998 |
| WO | WO-99/47674 | 9/1999 |

OTHER PUBLICATIONS

Wells, Biochemistry, vol. 29, pp. 8509-8517, 1990.*
Seffernick et al., J. Bacteriology, vol. 183, pp. 2405-2410, 2001.*
GenBank Accession No. I35613 (1997).
GenBank Accession No. AAB38703 (1996).
GenBank Accession No. U77035 (1997).
GenBank Accession No. CAA66950 (1998).
GenBank Accession No. U46767 (1997).
GenBank Accession No. D86955 (1997).
GenBank Accession No. X98306 (1998).
GeneSeq Accession No. W17660 (1997).
GeneSeq Accession No. R95690 (1996).
GeneBank Accession No. U64197 (1997).
GeneSeq Accession No. W44398 (1998).
GeneSeq Accession No. W61279 (1998).
GeneSeq Accession No. W57475 (1998).
GeneSeq Accession No. T90880 (1998).
GeneSeq Accession No. V28591 (1998).
GeneSeq Accession No. T90883 (1998).
GeneBank Accession No. W30191 (1998).
GenBank Accession No. AAC50943.1 (Aug. 6, 1996).
GenBank Accession No. AAB61534.1 (Aug. 6, 1996).

(Continued)

*Primary Examiner*—Hope Robinson
(74) *Attorney, Agent, or Firm*—Human Genome Sciences, Inc.

(57) ABSTRACT

Human chemokine polypeptides and DNA (RNA) encoding such chemokine polypeptides and a procedure for producing such polypeptides by recombinant techniques is disclosed. Also disclosed are methods for utilizing such chemokine polypeptides for the treatment of leukemia, tumors, chronic infections, autoimmune disease, fibrotic disorders, wound healing and psoriasis. Antagonists against such chemokine polypeptides and their use as a therapeutic to treat rheumatoid arthritis, autoimmune and chronic inflammatory and infective diseases, allergic reactions, prostaglandin-independent fever and bone marrow failure are also disclosed. Diagnostic assays for identifying mutations in nucleic acid sequence encoding a polypeptide of the present invention and for detecting altered levels of the polypeptide of the present invention are also disclosed.

8 Claims, 3 Drawing Sheets

OTHER PUBLICATIONS

GenBank Accession No. AA739063 (Jan. 14, 1998).
GenBank Accession No. T27336 (Dec. 6, 1994).
GenBank Accession No. AI735669 (Jun. 14, 1999).
GenBank Accession No. T27433 (Dec. 6, 1994).
GenBank Accession No. D31065 (Feb. 8, 1995).
GenBank Accession No. AA297433 (Apr. 18, 1997).
GenBank Accession No. AJ001634 (Sep. 10, 1997).
GenBank Accession No. AJ000979 (Jun. 30, 1997).
GenBank Accession No. AC002482 (Aug. 21, 1997).
GenBank Accession No. Z77650 (Jul. 30, 1996).
GenBank Accession No. Z77651 (Jul. 30, 1996).
GenBank Accession No. CAA04888 (Sep. 10, 1997).
GenBank Accession No. CAB01111 (Jul. 30, 1996).
GenBank Accession No. CAB01112 (Jul. 30, 1996).
GenBank Accession No. AI925360 (Jul. 30, 1999).
GenBank Accession No. AA403048 (Apr. 29, 1997).
GenBank Accession No. AA404346 (Apr. 30, 1997).
GenBank Accession No. AA426245 (May 19, 1997).
GenBank Accession No. T64134 (Feb. 17, 1995).
GenBank Accession No. T64262 (Feb. 17, 1995).
GenBank Accession No. D17181 (Jul. 21, 1993).
GeneSeq Accession No. AAR93087 (1994).
GeneSeq Accession No. AAW22670 (1996).
GeneSeq Accession No. AAW56087 (1996).
GeneSeq Accession No. AAW56690 (1996).
GeneSeq Accession No. AAR29479 (1991).
Adema et al., "A dendritic-cell-derived C-C chemokine that preferentially attracts naive T cells," *Nature* 387:713-717 (Jun. 1997).
Berger, M.S., "Isolation of Monocyte Chemotactic Protein-4," *Clinical Res.* 42(2):305A (1994).
Bischoff et al., "Monocyte Chemotactic Protein 1 Is a Potent Activator of Human Basophils," *J. Exp. Med.* 175:1271-1275 (May 1992).
Blum et al., "Three Human Homologs of a Murine Gene Encoding an Inhibitor of Stem Cell Proliferation," *DNA and Cell Biol.* 9(8)589-602 (1990).
Brown et al., "A Family of Small Inducible Proteins Secreted by Leukocytes are Members of a New Superfamily that Includes Leukocyte and Fibroblast-Derived Inflammatory Agents, Growth Factors, and Indicators of Various Activation Processes," *J. Immunol.* 142(2):679-687 (Jan. 15, 1989).
Clements et al., "Biological and Structural Properties of MIP-1a Expressed in Yeast," *Cytokine* 4(1):76-82 (Jan. 1992).
Craddock et al., "Antibodies to VLA4 integrin mobilize long-term repopulating cells and augment cytokine-induced mobilization in primates and mice," *Blood* (90(12):4779-4788 (Dec. 15, 1997).
Derynck et al., "Recombinant Expression, Biochemical Charcterization, and Biological Activities of Human MGSA/gro Protein," *Biochem.* 29(44):10225-10233 (1990).
Furuta et al., "Production and Characterization of Recombinant Human Neutrophil Chemotactic Factor," *J. Biochem.* 106:436441 (1989).
Garcia-Zepeda et al., "Human monocyte chemoattractant protein (MCP)-4 is a novel CC chemokine with activities on monocytes, eosinophils, and basophils induced in allergic and nonallergic inflammation that signals through the CC chemokine receptors (CCR)-2 and -3," *J. Immunol.* 157(12):5613-5626 (Dec. 15, 1996).
George et al., "Current Methods in Sequence Comparison and Analysis, Macromolecular Sequencing & Synthesis," *Alan R. Liss, Inc.* 12:127-149 (1988).
Glover, David M., "Gene Cloning," *Chapman and Hall* (1984).
Graham et al., "SCI/MIP-1a: A Potent Stem Cell Inhibitor with Potential Roles in Development," *Develop. Biol.* 151:377-381 (1992).
Hieshima et al., "A Novel Human CC Chemokine PARC That Is Most Homologous to Macrophage-Inflammatory Protein-1a/LD78a and Chemotactic for T Lymphocytes, but Not for Monocytes," *J. Immunol.* 159:1140-1149 (1997).
Hieshima et al., "Molecular Cloning of a Novel Human CC Chemokine Liver and Activation-regulated Chemokine (LARC) Expressed in Liver," *J. Biol. Chem.* 272(9):5846-5853 (Feb. 28, 1997).
Hromas et al., "Cloning and Characterization of Exodus, a Novel β-Chemokine," *Blood* 89(9):3315-3322 (1997).
Jose et al., "Eotaxin: A Potent Eosinophil Chemoattractant Cytokine Detected in a Guinea Pig Model of Allergic Airways Inflammation," *J. Exp. Med.* 179: 881-887 (Mar. 1994).
Kodelja et al., "Alternative Macrophage Activation-Associated CC-Chemokine-1, a Novel Structural Homologue of Macrophage Inflammatory Protein-1a with a TH2-Associated Expression Pattern," *J. Immunol.* 160(3):1411-1418 (Feb. 1, 1998).
Kuna et al., "Monocyte Chemotactic and Activating Factor Is a Potent Histamine-releasing Factor for Human Basophils," *J. Exp. Med.* 175:489-493 (Feb. 1992).
Kurdowska et al., "Biological and Kinetic Characterization of Recombinant Human Macrophage Inflammatory Peptides 2 Alpha and Beta and Comparison with the Neutrophil Activating Peptide 2 and Interleukin 8," *Cytokine* 6(2):124-134 (Mar. 1994).
Kwon et al., "cDNA sequences of two inducible T-cell genes," *PNAS USA* 86:1963-1967 (1989).
Laterveer et al., "Rapid mobilization of hematopoietic progenitor cells in rhesus monkeys by a single intravenous injection of interleukin-8," *Blood* 87(2):781-788 (Jan. 15, 1996).
Laterveer, L., et al., "Improved survival of lethally irradiated recipient mice transplanted with circulating progenitor cells mobilized b y IL-8after pretreatment with stem cell factor," *Exp. Hematol.* 24:1387-1393 (1996).
Lerner, Richard A., "Tapping the immunological repertorie to produce antibodies of predetermined specificity," *Nature* 299:592-596 (Oct. 14, 1982).
Liu et al., "The granulocyte colony-stimulating factor is required for the mobilization of murine hematopoietic progenitors into peripheral blood by cyclophosphamide or interleukin-8 but not flt-3 ligand," *Blood* 90(7):2522-2528 (Oct. 1, 1997).
Lukacs et al., "The Role of Macrophage Inflammatory Protein 1a in Schistosoma mansoni," *J. of Exp. Med.* 177:1551-1559 (Jun. 1993).
Matsushima et al., "Purification and Characterization of a Novel Monocyte Chemotactic and Activating Factor Produced by a Human Myelomonocytic Cell Line," *J. Exp. Med.* 169:1485-1490 (Apr. 1989).
Nakao et al., "Stuctures of Human Genes Coding for Cytokine LD78 and Their Expression," *Molec. Cell. Ciol.* 10(7):3646-3658 (Jul. 1990).
Obaru et al., "A cDNA Clone Used to Study mRNA Inducible in Human Tonsillar Lymphocytes by a Tumor Promoter," *J. Biochem.* 99(3):885-894 (1986).
Opdennaker et al., "Human monocyte chemotactic protein-3 (MCP-3): molecular cloning of he cDNA and comparison with other chemokines," *Biochem. Biophys. Res. Commun.* 191(2)535-542 (Mar. 15, 1993).
Patel et al. "Molecular and functional characterization of two novel human C-C chemokines as inhibitors of two distinct classes of myeloid progenitors," *J. Exp. Med.* 185(7):1163-1172 (Apr. 7, 1997).
Schall, Thomas J., "Biology of the RANTES/SIS Cytokine Family," *Cytokine* 3(3):165-183 (May 1991).
Schall et al., "Molecular cloning and expression of the murine RANTES cytokine: structural and functional conservation between mouse and man," *Eur. J. Immunol.* 22:1477-1481 (Jun. 1992).
Sudo et al., "2058 Expressed Sequence Tags (ESTs) from a Human Fetal Lung cDNA Library," *Genomics* 24:276-279 (1994).
Taub et al., "Chemokines, inflammation and the immune system," *Ther. Immunol.* 1(4):229-246 (Aug. 1994).
Uguccioni et al., "Monocyte Chemotacic Protein 4 (MCP-4), a Novel Structural and Functional Analogue of MCP-3 and Eotaxin," *J. Exp. Med.* 183:2379-2384 (May 1996).
Wolpe et al., Lab. of Med. Biochem., Rockefeller Univ. Press, New York USA, 175:3446-3658 (1990).
Widmer, et al., Genomic Cloning and Promoter Analysis of Macrophage Inflammatory Protein (MIP)-2, MIP-1a, and MIP-1β, Members of the Chemokine Superfamily of Proinflammatory Cytokines, *J. Immunol.* 150(11):4996-5012 (Jun. 1, 1993).

Zipfel et al., "Mitogenic Activation of Human T Cells Induces Two Closely Related Genes Which Share Structural Similarities with a New Family of Secreted Factors," *J. Immunol.*, 142(5):1582-1590 (Mar. 1, 1989).

Lin et al., "Selective early production of CCL20, or macrophage inflammatory protein 3alpha, by human mast cells in response to *Pseudomonas aeruginosa*," *Infect. Immun.*, 71(1):365-373 (Jan. 2003).

Nishi et al., "Involvement of Myeloid Dendritic Cells in the Development of Gastric Secondary Lymphoid Follicles in Helicobacter pylori-Infected Neonatally Thymectomized BALB/c Mice," *Infect. Immun.*, 71(4):2153-2162 (Apr. 2003).

Sierro et al., "Flagellin stimulation of intestinal epithelial cells triggers CCL20-mediated migration of dendritic cells," *PNAS*, 98(24):13722-13727 (Nov. 20, 2001).

Bennouna et al., "Cross-Talk in the Innate Immune System: Neutrophils Instruct Recruitment and Activation of Dendritic Cells during Microbial Infection," *J. Immunol.*, 171:6052-6058 (2003).

Hoover et al., "The Structure of Human Macrophage Inflammatory Protein-3alpha/CCL20—Linking Antimicrobial and CC Chemokine Receptor-6-Binding Activities With Human Beta-Defensins," *J. Biol. Chem.*, 277940):37647-37654 (Oct. 4, 2002).

Yang et al., "Many chemokines including CCL20/MIP-3alpha display antimicrobial activity," *J. Leukoc. Biol.*, 74(3):448-455 (Sep. 2003).

Matsui et al., "Seelctive recruitment of CCR6-expressing cells by increased production of MIP-3 alpha in rheumatoid arthritis," *Clin. Exp. Immunol.*, 125(1):155-161 (Jul. 2001).

Ruth et al., "Role of macrophage inflammatory protein-3alpha and its ligand CCR6 in rheumatoid arthritis," *Lab. Invest.*, 83(4):579-588 (Apr. 2003).

Kwon et al., "Role of macrophage inflammatory protein-3alpha and its ligand CCR6 in rheumatoid artritis," *Lab. Invest.*, 83(4):579-588 (Apr. 2003).

Ambrosini et al., "A Role for Macrophage Inflammatory Protein-3alpha/CC Chemokine Ligand 20 in Immune Priming During T Cell-Mediated Inflammation of the Central Nervous System," *J. Immunol.*, 170:6298-6306 (2003).

Kohler et al., "A Role for Macrophage Inflammatory Protein-3alpha/CC Chemokine Ligand 20 in Immune Priming During T Cell-Mediated Inflammation of the Central Nervous System," *J. Immunol.*, 170:6298-6306 (2003).

Fushimi et al., "Macrophage inflammatory protein 3alpha transgene attracts dendritic cells to established murine tumors and suppresses tumor growth," *J. Clin. Invest.*, 105(10):1383-1393 (May 2000).

Crittenden et al., "Expression of Inflammatory Chemokines Combined with Local Tumor Destruction Enhances Tumor Regression and Long-term Immunity," *Cancer Res.*, 63:5505-5512 (Sep. 1, 2003).

Abiko et al., "Expression of MIP-3alpha/CCL20, a macrophage inflammatory protein in oral squamous cell carcinoma," *Arch. Oral Biol.*, 48(2):171-175 (Feb. 2003).

Akahoshi et al., "Production of Macrophage Inflammatory Protein 3 (MIP-3) (CCL20) and MIP-3 (CCL190 by Human Peripheral Blood Neutrophils in Response to Microbial Pathogens," *Infect. Immun.*, 71(1):524-526 (Jan. 2003).

Dieu-Nosjean et al., "Macrophage Inflammatory Protein 3 Is Expressed at Inflamed Epithelial Surfaces and Is the Most Potent Chemokine Known in Attracting Langerhans Cell Precursors," *J. Exp. Med.*, 192(5):705-717 (Sep. 2002).

Homey et al., "Up-Regulation of Macrophage Inflammatory Protein-3/CCL20 and CC Chemokine Receptor 6 in Psoriasis," *J. Immunol.*, 164:6621-6632 (2000).

Hosokawa et al., "Macrophage inflammatory protein 3alpha-CC chemokine receptor 6 interactions play an important role in CD4+ T-cell accumulation in periodontal diseased tissue," *Clin. Exp. Immunol.*, 128(3):548-554 (Jun. 2002).

Kleeff et al., "Detection and localization of Mip-3alpha/LARC/ Exodus, a macrophage proinflammatory chemokine, and its CCR6 receptor in human pancreatic cancer," *Int. J. Cancer*, 81(4):650-657 (May 17, 1999).

Skolnick et al., "Structural genomics and its importance for gene function analysis," Nature Biotechnol., 18:283-287 (Mar. 2000).

\* cited by examiner

ATGTGCTGTGTACCAAGAGTTTGCTCCTGGCTGCTTTGATGTCAGTGCTGCTACTCCACCTC
 M  C  C  T  K  S  L  L  L  A  A  L  M  S  V  L  L  L  H  L

TGCGGGCCAATCAGGAACAAGCAGCAACTTTGACTGCTGTCTTGGATACAGACCGTATT
 C  G  E  S  E  A  A  S  N  F  D  C  C  L  G  Y  T  D  R  I

CTTCATCCTAAATTTATTGTGGGCTTCACACGGCAGCTGGCCAATGAAGGCTGTGACATC
 L  H  P  K  F  I  V  G  F  T  R  Q  L  A  N  E  G  C  D  I

AATGCTATCATCTTTCACACAAAGAAAAAGTTGTCTGTGTGCGCAAATCCAAAACAGACT
 N  A  I  I  F  H  T  K  K  K  L  S  V  C  A  N  P  K  Q  T

TGGGTGAAATATATTGTGCGTCTCCTCAGTAAAAAGTCAAGAACATGTAA
 W  V  K  Y  I  V  R  L  L  S  K  K  V  K  N  M  *

FIG. 1

ATGAAAGTTTCTGCAGTGCTTCTGTGCCTGCTCATGACAGCAGCTTTCAACCCCCAG
 M  K  V  S  A  V  L  L  C  L  L  M  T  A  A  F  N  P  Q

GGACTTGCTCAGCCAGATGCACTCAACGTCCCCATCTACTTGCTCTTCACATTAGCAGT
 G  L  A  Q  P  D  A  L  N  V  P  S  T  C  C  F  T  S  S

AAGAAGATCTCCTTGCAGAGGCTGAAGAGCTATGTGATCACCACCAGCAGGTGTCCCAG
 K  K  I  S  L  Q  R  L  K  S  Y  V  I  T  T  S  R  C  P  Q

AAGGCTGTCATCTTCAGAACCAAACTGGGCAAGGAGATCTGTGCTGACCCAAAGGAGAAG
 K  A  V  I  F  R  T  K  L  G  K  E  I  C  A  D  P  K  E  K

TGGGTCCAGAATTATATGAAACACCTGGGCCGAAAGCTCACACCCTGAAGACTTGA
 W  V  Q  N  Y  M  K  H  L  G  R  K  A  H  T  L  K  T  *

FIG. 2

```
EAASNFDCCLGYTDRILHPKFIVGFTRQLANEGCDINAIIFHTKKKLSVC
 ::  ::  |:  . |:  .  .  . ||:.. |. . :
HPGIPSACCFRVTNICKISFQALKSYKIITSSKCPQTAIVFEIKPDKMIC

ANPKQTWVKYIVRLLSKKVK   94
|:|:  .||   ||.   .:|...  .
ADPRXXWVQDAKKYLDQISQ   70
```

FIG. 3

```
MKVSAVLLCLLLMTAAFNPQGLAQPDALNVPSTCCFTFSSKKIISLQRLKS
||. || .|| ||||||| .||.|||| ::|...|| |||. | |||.  |..|
MKASAALLCLLLTAAAFSPQGLAQPVGINTSTTCCYRFINKKIPKQRLES

YVITT.SRCPQKAVIFRTKLGKEICADPKEKWVQNYMKHLGRKAHTLKT
| |  :|| ||||||:||||||||||| :|||:  |||| | | :|..:|   |||
YRRTTSSHCPREAVIFKTKLDKEICADPTQKWVQDFMKHLDKKTQTPKL
```

HUMAN CKβ-10 POLYNUCLEOTIDES

CROSS REFERENCE TO RELATED APPLICATIONS

This Application is a divisional of U.S. application Ser. No. 10/164,621, filed Jun. 10, 2002 (now U.S. Pat. No. 6,921,645), issued Jul. 26, 2005, which is a divisional of U.S. application Ser. No. 09/261,201, filed Mar. 3, 1999 (now U.S. Pat. No. 6,458,349, issued Oct. 1, 2002), which is a divisional of U.S. application Ser. No. 08/458,355, filed Jun. 2, 1995 (now U.S. Pat. No. 5,981,230, issued Nov. 9, 1999), which is a continuation-in-part of International Application No. PCT/US94/09484, filed Aug. 23, 1994, each of which is hereby incorporated by reference in its entirety.

FIELD OF THE INVENTION

This invention relates to newly identified polynucleotides, polypeptides encoded by such polynucleotides, the use of such polynucleotides, the use of such polynucleotides and polypeptides, as well as the production of such polynucleotides and polypeptides. More particularly, the polypeptides of the present invention are human chemokine beta-4 and human chemokine beta-10, sometimes hereinafter referred to as "Ckβ-4" and "Ckβ-10", collectively referred to as "the chemokine polypeptides". The invention also relates to inhibiting the action of such polypeptides.

BACKGROUND OF THE INVENTION

Chemokines are an emerging super-family of small secreted cytokines that are structurally and functionally related. All chemokines exhibit 25 to 75% homology at the amino acid level and contain spatially conserved cysteine residues as do the polypeptides of the present invention. Members of the "C—X—C branch" (according to the position of the first two cysteines in the conserved motif), also known as neutrophil-activating peptide (NAP)/IL-8 family, exert pro-inflammatory activity mainly through their action on neutrophils (e.g., IL-8 and NAP-2), whereas members of the "C—C branch" family appear to attract certain mononuclear cells. Members of the "C—C branch" include PF4, MIPs, MCPs, and the chemokine polypeptides of the present invention.

Numerous biological activities have been assigned to this chemokine family. The macrophage inflammatory protein 1α and 1β are chemotactic for distinct lymphocyte populations and monocytes (Schall, T. J., Cytokine, 3:165 (1991)), while MCP-1 has been described as a specific monocyte chemo-attractant (Matsushima, K., et al., J. Exp. Med., 169:1485 (1989)). The common function of this chemokine family is their ability to stimulate chemotactic migration of distinct sets of cells, for example, immune cells (leukocytes) and fibroblasts. These chemokines are also able to activate certain cells in this family.

The immune cells which are responsive to the chemokines have a vast number of in vivo functions and therefore their regulation by such chemokines is an important area in the treatment of disease.

For example, eosinophils destroy parasites to lessen parasitic infection. Eosinophils are also responsible for chronic inflammation in the airways of the respiratory system. Macrophages are responsible for suppressing tumor formation in vertebrates. Further, basophils release histamine which may play an important role in allergic inflammation. Accordingly, promoting and inhibiting such cells, has wide therapeutic application.

BRIEF SUMMARY OF THE INVENTION

In accordance with one aspect of the present invention, there are provided novel polypeptides which are Ckβ-4, and Ckβ-10, as well as fragments, analogs and derivatives thereof. The polypeptides of the present invention are of human origin.

In accordance with another aspect of the present invention, there are provided polynucleotides (DNA or RNA) which encode such polypeptides.

In accordance with yet a further aspect of the present invention, there is provided a process for producing such polypeptides by recombinant techniques.

In accordance with yet a further aspect of the present invention, there is provided a process for utilizing such polypeptides, or polynucleotides encoding such polypeptides for therapeutic purposes, for example, to treat solid tumors, chronic infections, auto-immune diseases, psoriasis, asthma, allergy, to regulate hematopoiesis, and to promote wound healing.

In accordance with yet a further aspect of the present invention, there are provided antibodies against such polypeptides.

In accordance with yet another aspect of the present invention, there are provided antagonists to such polypeptides, which may be used to inhibit the action of such polypeptides, for example, in the treatment of auto-immune diseases, chronic inflammatory and infective diseases, histamine-mediated allergic reactions, prostaglandin-independent fever, bone marrow failure, silicosis, sarcoidosis, hyper-eosinophilic syndrome and lung inflammation.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 displays the cDNA sequence (SEQ ID NO:1) and corresponding deduced amino acid sequence (SEQ ID NO:2) of Ckβ-4. The initial 24 amino acids represent the deduced leader sequence of Ckβ-4 such that the putative mature polypeptide comprises 72 amino acids. The standard one-letter abbreviation for amino acids is used.

FIG. 2 displays the cDNA sequence (SEQ ID NO:3) and corresponding deduced amino acid sequence (SEQ ID NO:4) of Ckβ-10. The initial 23 amino acids represent the putative leader sequence of Ckβ-10 such that the putative mature polypeptide comprises 75 amino acids. The standard one-letter abbreviation for amino acids is used.

FIG. 3 displays the amino acid sequence homology between Ckβ-4 (top; SEQ ID NO:2) and the mature peptide of eotaxin (bottom; SEQ ID NO:15).

FIG. 4 displays the amino acid sequence homology between Ckβ-10 (top; SEQ ID NO:4) and human MCP-3 (bottom; SEQ ID NO:16).

DETAILED DESCRIPTION

In accordance with an aspect of the present invention, there are provided isolated nucleic acids (polynucleotides) which encode for the mature polypeptides having the deduced amino acid sequences of FIGS. 1 and 2 (SEQ ID NOS:2 and 4) or for the mature polypeptide encoded by the cDNA of the clone deposited with the American Type Tissue Culture Collection ("ATCC") on Jul. 29, 1994 as ATCC Deposit No. 75848 (Ckβ-4) and ATCC Deposit No. 75849 (Ckβ-10). The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

The polynucleotide encoding Ckβ-4 was discovered in a cDNA library derived from a human gall bladder. Ckβ-4 is structurally related to the chemokine family. It contains an open reading frame encoding a protein of 96 amino acid residues of which approximately the first 24 amino acids residues are the putative leader sequence such that the mature protein comprises 72 amino acids. The protein exhibits the highest degree of homology to eotaxin with 20% identity and 37% similarity over the entire coding sequence. It is also important that the four spatially conserved cysteine residues in chemokines are found in the polypeptides of the present invention.

The polynucleotide encoding Ckβ-10 was discovered in a cDNA library derived from nine week early human tissue. Ckβ-10 is structurally related to the chemokine family. It contains an open reading frame encoding a protein of 98 amino acid residues of which approximately the first 23 amino acids residues are the putative leader sequence such that the mature protein comprises 75 amino acids. The protein exhibits the highest degree of homology to MCP-3 with 65% identity and 77% similarity over the entire coding sequence.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptides may be identical to the coding sequence shown in FIGS. 1 and 2 or that of the deposited clones or may be a different coding sequence which coding sequence, as a result of the redundancy or degeneracy of the genetic code, encodes the same mature polypeptides as the DNA of FIGS. 1 and 2 or the deposited cDNAs.

The polynucleotides which encode for the mature polypeptides of FIGS. 1 and 2 or for the mature polypeptides encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptides.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1 and 2 or the polypeptide encoded by the cDNA of the deposited clones. The variant of the polynucleotides may be a naturally occurring allelic variant of the polynucleotides or a non-naturally occurring variant of the polynucleotides.

Thus, the present invention includes polynucleotides encoding the same mature polypeptides as shown in FIGS. 1 and 2 or the same mature polypeptides encoded by the cDNA of the deposited clones as well as variants of such polynucleotides which variants encode for a fragment, derivative or analog of the polypeptides of FIGS. 1 and 2 or the polypeptides encoded by the cDNA of the deposited clones. Such nucleotide variants include deletion variants, substitution variants and addition or insertion variants.

As hereinabove indicated, the polynucleotides may have a coding sequence which is a naturally occurring allelic variant of the coding sequence shown in FIGS. 1 and 2 or of the coding sequence of the deposited clones. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptides may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptides of the present invention. The marker sequence may be a hexa-histidine tag supplied by a pQE-9 vector to provide for purification of the mature polypeptides fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequence (introns) between individual coding segment (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferable have at least 30 bases and may contain, for example, 50 or more bases. The probe may also be used to identify a cDNA clone corresponding to a full length transcript and a genomic clone or clones that contain the complete gene including regulatory and promoter regions, exons and introns. An example of a screen comprises isolating the coding region of the gene by using the known DNA sequence to synthesize an oligonucleotide probe. Labeled oligonucleotides having a sequence complementary to that of the gene o the present invention are used to screen a library of human cDNA, genomic DNA or mRNA to determine which members of the library the probe hybridizes to.

The present invention further relates to polynucleotides which hybridize to the hereinabove-described sequences if there is at least 90% and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1 and 2 (SEQ ID NO: 1 and 3) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO: 1, for example, for recovery of the polynucleotide or as a diagnostic probe or as PCR primer.

Thus, the present invention is directed to polynucleotides having at least a 90% and more preferable at least a 95% identity to a polynucleotide which encodes the polypeptide of SEQ ID NO: 2 and 4 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. § 112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to chemokine polypeptides which have the deduced amino acid sequences of FIGS. 1 and 2 or which has the amino acid sequence encoded by the deposited cDNA, as well as fragments, analogs and derivatives of such polypeptides.

The terms "fragment," "derivative" and "analog" when referring to the polypeptides of FIGS. 1 and 2 or that encoded by the deposited cDNA, means polypeptides which retain essentially the same biological function or activity as such polypeptides. Thus, an analog includes a proprotein which can be activated by cleavage of the proprotein portion to produce an active mature polypeptide.

The chemokine polypeptides of the present invention may be recombinant polypeptides, natural polypeptides or a synthetic polypeptides, preferably recombinant polypeptides.

The fragment, derivative or analog of the polypeptides of FIGS. 1 and 2 or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 and 4 (in particular the mature polypeptide) as well as polypeptides which have at least 70% similarity (preferably at least 70% identity) to the polypeptide of SEQ ID NO:2 and 4 and more preferably at least 90% similarity (more preferably at least 90% identity) to the polypeptide of SEQ ID NO: 2 and 4 and still more preferably at least 95% similarity (still more preferably at least 90% identity) to the polypeptide of SEQ ID NO:2 and 4 and also include portions of such polypeptides with such portions of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the Ckβ-4 and Ckβ-10 genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.\ coli$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.\ coli$.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as $E.\ coli$, $Streotomyces$, $Salmonella\ typhimurium$; fungal cells, such as yeast; insect cells such as $Drosophila$ and $Spodoptera$ Sf9; animal cells such as CHO, COS or Bowes melanoma; adenoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, PBLUESCRIPT® SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of $E.\ coli$ and $S.\ cerevisiae$ TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The chemokine polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

The chemokine polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The chemokine polypeptides may be used to inhibit bone marrow stem cell colony formation as adjunct protective treatment during cancer chemotherapy and for leukemia.

The chemokine polypeptides may also be used to inhibit epidermal keratinocyte proliferation for treatment of psoriasis, which is characterized by keratinocyte hyper-proliferation.

The chemokine polypeptides may also be used to treat solid tumors by stimulating the invasion and activation of host defense cells, e.g., cytotoxic T cells and macrophages. They may also be used to enhance host defenses against resistant chronic infections, for example, mycobacterial infections via the attraction and activation of microbicidal leukocytes.

The chemokine polypeptides may also be used to treat auto-immune disease and lymphocytic leukemias by inhibiting T cell proliferation by the inhibition of IL2 biosynthesis.

Ckβ-4 and Ckβ-10 may also be used in wound healing, both via the recruitment of debris clearing and connective tissue promoting inflammatory cells and also via its control of excessive TGFβ-mediated fibrosis. In this same manner, Ckβ-4 and Ckβ-10 may also be used to treat other fibrotic disorders, including liver cirrhosis, osteoarthritis and pulmonary fibrosis. The chemokine polypeptides also increase the presence of eosinophils which have the distinctive function of killing the larvae of parasites that invade tissues, as in schistosomiasis, trichinosis and ascariasis. They may also be used to regulate hematopoiesis, by regulating the activation and differentiation of various hematopoietic progenitor cells.

Chemokines may also be employed as inhibitors of angiogenesis, therefore, they have anti-tumor effects.

This invention provides a method for identification of the receptor for the polypeptides of the present invention. The gene encoding the receptors can be identified by expression cloning. Briefly, polyadenylated RNA is prepared from a cell responsive to the polypeptide of the present invention and a cDNA library created from this RNA is divided into pools and used to transfect COS cells or other cells that are not responsible to the polypeptide of the present invention. Transfected cells which are grown on glass slides are exposed to labeled polypeptides of the present invention. The polypeptides can be labeled by a variety of means including iodidation or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding and single clone that encodes the putative receptor. As an alternative approach for receptor identification, labeled ligand can be photoaffinity linked with cell membrane or extract preparations that express the receptor molecule. Cross-linked material is resolved by PAGE and exposed to x-ray film. The labeled complex containing the polypeptide-receptor can be excised, resolved into peptide fragments, and subjected to protein microsequencing. The amino acid sequence obtained from microsequencing would be used to design a set of generate oligonucleotide probes to screen a cDNA library to identify the gene encoding the putative receptor.

This invention also provides a method of screening compounds to identity those which bind to the receptor and elicit a second messenger response (agonist) or do not elicit a second messenger response (antagonist). As an example, a mammalian cell or membrane preparation expressing the receptor would be incubated with a labeled compound. The response of the known second messenger system following interaction of the compound and the receptor is then measured. Such second messenger systems include but are not limited to, cAMP guanylate cyclase, ion channels or phosphoinositide hydrolysis.

Potential antagonists include antibodies, or in some cases, oligonucleotides, which bind to the polypeptides. Another example of a potential antagonist is a negative dominant mutant of the polypeptides. Negative dominant mutants are polypeptides which bind to the receptor of the wild-type polypeptide, but fail to retain biological activity.

An assay to detect negative dominant mutants of the polypeptides include an in vitro chemotaxis assay wherein a multiwell chemotaxis chamber equipped with polyvinylpyrrolidone-free polycarbonate membranes is used to measure the chemoattractant ability of the polypeptides for leukocytes in the presence and absence of potential antagonist/inhibitor or agonist molecules.

Antisense constructs prepared using antisense technology are also potential antagonists. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple-helix, see Lee et al., Nucl. Acids Res., 6:3073 (1979); Cooney et al, Science, 241:456 (1988); and Dervan et al., Science, 251:1360 (1991)), thereby preventing transcription and the production of the polypeptides. The antisense RNA oligonucleotide hybridizes to the mRNA in vivo and blocks translation of the mRNA molecule into the polypeptides (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of the polypeptides.

Another potential antagonist is a peptide derivative of the polypeptides which are naturally or synthetically modified analogs of the polypeptides that have lost biological function yet still recognize and bind to the receptors of the polypeptides to thereby effectively block the receptors. Examples of peptide derivatives include, but are not limited to, small peptides or peptide-like molecules.

The antagonists may be employed to inhibit the chemotaxis and activation of macrophages and their precursors, and of neutrophils, basophils, B lymphocytes and some T cell subsets, e.g., activated and CD8 cytotoxic T cells and natural killer cells, in auto-immune and chronic inflammatory and infective diseases. Examples of auto-immune diseases include rheumatoid artritis, multiple sclerosis, and insulin-dependent diabetes. Some infectious diseases include silicosis, sarcoidosis, idiopathic pulmonary fibrosis by preventing the recruitment and activation of mononuclear phagocytes, idiopathic hyper-eosinophilic syndrome by preventing eosinophil production and migration, endotoxic shock by preventing the migration of macrophages and their production of the chemokine polypeptides of the present invention.

The antagonists may also be employed for treating atherosclerosis, by preventing monocyte infiltration in the artery wall.

The antagonists may also be employed to treat histamine-mediated allergic reactions by inhibiting chemokine-induced mast cell and basophil degranulation and release of histamine.

The antagonists may also be employed to treat inflammation by preventing the attraction of monocytes to a wound area. They may also be employed to regulate normal pulmonary macrophage populations, since acute and chronic inflammatory pulmonary diseases are associated with sequestration of mononuclear phagocytes in the lung.

Antagonists may also be employed to treat rheumatoid arthritis by preventing the attraction of monocytes into synovial fluid in the joints of patients. Monocyte influx and activation plays a significant role in the pathogenesis of both degenerative and inflammatory arthropathies.

The antagonists may be employed to interfere with the deleterious cascades attributed primarily to IL-1 and TNF, which prevents the biosynthesis of other inflammatory cytokines. In this way, the antagonists may be employed to prevent inflammation. The antagonists may also be employed to inhibit prostaglandin-independent fever induced by chemokines.

The antagonists may also be employed to treat cases of bone marrow failure, for example, aplastic anemia and myelodysplastic syndrome.

The antagonists may also be employed to treat asthma and allergy by preventing eosinophil accumulation in the lung. The antagonists may be employed in a composition with a pharmaceutically acceptable carrier, e.g., as hereinafter described.

The chemokine polypeptides and agonists or antagonists of the present invention may be employed in combination with a suitable pharmaceutical carrier. Such compositions comprise a therapeutically effective amount of the polypeptide, agonist and antagonist and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides agonist and antagonist of the present invention may be employed in conjunction with other therapeutic compounds.

The pharmaceutical compositions may be administered in a convenient manner such as by the topical, intravenous, intraperitoneal, intramuscular, intratumor, subcutaneous, intranasal or intradermal routes. The polypeptides are administered in an amount which is effective for treating and/or prophylaxis of the specific indication. In general, the polypeptides will be administered in an amount of at least about 10 μg/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

The chemokine polypeptides and agonists or antagonists which are polypeptides may be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be employed to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus Retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus.

In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., Biotechniques, Vol. 7, No. 9, 980–990 (1989) or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytital virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoters; retroviral LTRs (including the modified retroviral LTRs hereinabove described); the β-actin promoter; and human growth hormone promoters. The promoter also may be the native promoter which controls the gene encoding the polypeptide. The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*. Vol. 1, pages 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cell, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the gene of the present invention as a diagnostic. Detection of a mutated form of the gene will allow a diagnosis of a disease or a susceptibility to a disease which results from underexpression of the polypeptides of the present invention.

Individuals carrying mutations in the gene of the present invention may be detected at the DNA level by a variety of techniques. Nucleic acids for diagnosis may be obtained from a patient's cells, including but not limited to blood, urine, Saliva, tissue, biopsy and autopsy material. The genomic DNA may be used directly for detection or may be amplified enzymatically by using PCR (Saiki et al., Nature, 324:163–166(1986)) prior to analysis. RNA or cDNA may also be used for the same purpose. As an example, PCR primers complementary to the nucleic acid encoding the polypeptides of the present invention can be used to identify and analyze mutations. For example, deletion and insertion can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by Rnase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PRC. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science 230:12242 (1995)).

Sequence changes at specific locations may also be revealed by nuclease protection assays, such as Rnase and S1 protection or the chemical cleavage method (e.g., Cotton et al., PNAS, USA, 85:4397–4402 (1985)).

Thus, the detection of a specific DNA sequence may be achieved by methods such as hybridization, Rnase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of the polypeptide of the present invention in various tissues since an over-expression of the proteins compared to normal control tissue samples can detect the presence of disorders of the host. Assays used to detect levels of the polypeptide of the present invention in a sample derived from a host are well-known to those of skill in the art and include radioimmunoassays, competitive-binding assays, Western Blot analysis and preferably an ELISA assay. An ELISA assay initially comprises preparing an antibody specific to a Ckβ-4 or 10 antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attached to the polypeptide of the present invention attached to the polystyrene dish. All unbound monoclonal antibody is washed out with buffer. The reporter antibody linked to horseradish peroxidase is now placed in the dish resulting in binding of the reporter antibody to any monoclonal antibody bound to the polypeptide of the present invention. Unattached reporter antibody is then washed out. Peroxidase substrates are then added to the dish and the amount of color developed in a given time period is a measurement of the amount of the polypeptide of the present invention present in a given volume of patient sample when compared against a standard curve.

A competition assay may be employed wherein antibodies specific to the polypeptide of the present invention are attached to a solid support and a labeled polypeptide of the present invention and a sample derived from the host are passed over the solid support and the amount of label detected attached to the solid support can be correlated to a quantity of the polypeptide of the present invention in the sample The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA having at least 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptides products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of Ckβ-4

The DNA sequence encoding for Ckβ-4, ATCC # 75848, is initially amplified using PCR oligonucleotide primers corresponding to the 5' and 3' sequences of the processed Ckβ-4 protein (minus the putative signal peptide sequence). Additional nucleotides corresponding to Ckβ-4 were added to the 5' and 3' sequences respectively. The 5' oligonucleotide primer has the sequence 5' CCCGCATGCAAGCAG-CAAGCAACTTT 3' (SEQ ID NO:5) contains a SphI restriction enzyme site (bold) followed by 17 nucleotides of Ckβ-4 coding sequence (underlined) starting from the second nucleotide of the sequences coding for the mature protein. The ATG codon is included in the SphI site. In the next codon following the ATG, the first base is from the SphI site and the remaining two bases correspond to the second and third base of the first codon of the putative mature protein. As a consequence, the first base in this codon is changed from G to C compared with the original sequences, resulting in an E to Q substitution in the recombinant protein. The 3' sequence, 5' AAAGGATCCCATGTTCT-TGACTTTTTTACT 3' (SEQ ID NO:6) contains complementary sequences to a BamH1 site (bold) and is followed by 21 nucleotides of gene specific sequences preceding the termination codon. The restriction enzyme sites correspond to the restriction enzyme sites on the bacterial expression vector pQE-70 (Qiagen, Inc. 9259 Eton Avenue, Chatsworth, Calif., 91311). pQE-70 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-70 was then digested with SphI and BamH1. The amplified sequences were ligated into pQE-70 and were inserted in frame with the sequence encoding for the histidine tag and the RBS. FIG. 8 shows a schematic representation of this arrangement. The ligation mixture was then used to transform the E. coli strain available from Qiagen under the trademark M15/rep 4 by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized Ckβ-4 was purified from this solution by chromatography on a Nickel-Chelate column under conditions that allow for tight binding by proteins containing the 6-His tag (Hochuli, E. et al., J. Chromatography 411:177–184 (1984)). Ckβ-4 (>98% pure) was eluted from the column in 6 molar guanidine HCl pH 5.0. Protein renaturation out of GnHCl can be accomplished by several protocols (Jaenicke, R. and Rudolph, R., Protein Structure—A Practical Approach, IRL Press, New York (1990)). Initially, step dialysis is utilized to remove the GnHCL. Alternatively, the purified protein isolated from the Ni-chelate column can be bound to a second column over which a decreasing linear GnHCL gradient is run. The protein is allowed to renature while bound to the column and is subsequently eluted with a buffer containing 250 mM Imidazole, 150 mM NaCl, 25 mM Tris-HCl pH 7.5 and 10% Glycerol. Finally, soluble protein is dialyzed against a storage buffer containing 5 mM Ammonium Bicarbonate.

EXAMPLE 2

Bacterial Expression and Purification of Ckβ-10

The DNA sequence encoding for Ckβ-10, ATCC # 75849, is initially amplified using PCR oligonucleotide primers corresponding to the 5' and 3' sequences of the processed Ckβ-10 protein (minus the signal peptide sequence) and the vector sequences 3' to the Ckβ-10 gene. Additional nucleotides corresponding to Ckβ-10 were added to the 5' and 3' sequences respectively. The 5' oligonucleotide primer has the sequence 5' CCCGCATGCAGCCAGATGCACT-CAACG 3' (SEQ ID NO:7) contains a SphI restriction enzyme site (bold) followed by 19 nucleotides of Ckβ-10 coding sequence (underlined) starting from the sequences coding for the mature protein. The ATG codon is included in the SphI site. The 3' sequence, 5' AAAGGATCCAGTCT-TCAGGGTGTGAGCT 3' (SEQ ID NO:8) contains complementary sequences to a BamH1 site (bold) and is followed by 19 nucleotides of gene specific sequences preceding the termination codon. The restriction enzyme sites correspond to the restriction enzyme sites on the bacterial expression vector pQE-70 (Qiagen, Inc. 9259 Eton Avenue, Chatsworth, Calif., 91311). pQE-70 encodes antibiotic resistance (Amp'), a bacterial origin of replication (ori), an IPTG-regulatable promoter operator (P/O), a ribosome binding site (RBS), a 6-His tag and restriction enzyme sites. pQE-70 was then digested with SphI and BamH1. The amplified sequences were ligated into pQE-70 and were inserted in frame with the sequence encoding for the histidine tag and the RBS. FIG. 10 shows a schematic representation of this arrangement. The ligation mixture was then used to transform the E. coli strain available from Qiagen under the trademark M15/rep 4 by the procedure described in Sambrook, J. et al., Molecular Cloning: A Laboratory Manual, Cold Spring Laboratory Press, (1989). M15/rep4 contains multiple copies of the plasmid pREP4, which expresses the lacd repressor and also confers kanamycin resistance (Kan'). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacd repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized Ckβ-10 was purified from this solution by chromatography on a Nickel-Chelate column under conditions that allow for tight binding by proteins containing the 6-His tag (Hochuli, E. et al., J. Chromatography 411:177–184 (1984)). Ckβ-10 (>98% pure) was eluted from the column in 6 molar guanidine HCl pH 5.0. Protein renaturation out of GnHCl can be accomplished by several protocols (Jaenicke, R. and Rudolph, R., Protein Structure—A Practical Approach, IRL Press, New York (1990)). Initially, step dialysis is utilized to remove the GnHCL. Alternatively, the purified protein isolated from the Ni-chelate column can be bound to a second column over which a decreasing linear GnHCL gradient is run. The protein is allowed to renature while bound to the column and is subsequently eluted with a buffer containing 250 mM Imidazole, 150 mM NaCl, 25 mM Tris-HCl pH 7.5 and 10% Glycerol. Finally, soluble protein is dialyzed against a storage buffer containing 5 mM Ammonium Bicarbonate. The protein was then analyzed on an SDS-PAGE gel

EXAMPLE 3

Expression of Recombinant Ckβ-4 in COS Cells

The expression of plasmid, Ckβ-4 HA is derived from a vector pcDNAI/Amp (Invitrogen) containing: 1) SV40 origin of replication, 2) ampicillin resistance gene, 3) E. coli replication origin, 4) CMV promoter followed by a polylinker region, a SV40 intron and polyadenylation site. A DNA fragment encoding the entire Ckβ-4 precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lemer, 1984, Cell 37, 767). The infusion of HA tag to the target protein allows easy detection of the recombinant protein with an antibody that recognizes the HA epitope.

The plasmid construction strategy is described as follows:

The DNA sequence encoding for Ckβ-4, ATTC. # 75848 was constructed by PCR on the original EST cloned using two primers: the 5' primer 5' GGAAAGCTTATGTGCTG-TACCAAGAGTTT 3' (SEQ ID NO:9) contains a HindIII site followed by 20 nucleotides of Ckβ-4 coding sequence starting from the initiation codon; the 3' sequence 5' CGCTCTAGATTAAGCGTAGTCTGG-GACGTCGTATGGGTAACA TGGTTCCTTGACTTTTT 3' (SEQ ID NO:10) contains complementary sequences to XbaI site, translation stop codon, HA tag and the last 20 nucleotides of the Ckβ-4 coding sequence (not including the stop codon). Therefore, the PCR product contains a HindIII site, Ckβ-4 coding sequence followed by HA tag fused in frame, a translation termination stop codon next to the HA tag, and an XbaI site. The PCR amplified DNA fragment and the vector, pcDNAI/Amp, were digested with HindIII and XbaI restriction enzyme and ligated. The ligation mixture was transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant Ckβ-4, COS cells were transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the Ckβ-4 HA protein was detected by radiolabelling and immunoprecipitation method. (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP40, 0.5% DOC, 50 mM Tris, pH 7.5). (Wilson, I. et al., Id. 37:767 (1984)). both cell lysate and culture media were precipitated with a HA specific monoclonal antibody. Proteins precipitated were analyzed by SDS-PAGE.

EXAMPLE 4

Expression of Recombinant Ckβ-10 in COS Cells

The expression of plasmid, Ckβ-10 HA is derived from a vector pcDNAI/Amp (Invitrogen) containing: 1) SV40 origin of replication, 2) ampicillin resistance gene, 3) *E.coli* replication origin, 4) CMV promoter followed by a polylinker region, a SV40 intron and polyadenylation site. A DNA fragment encoding the entire Ckβ-10 precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to the target protein allows easy detection of the recombinant protein with an antibody that recognizes the HA epitope.

The plasmid construction strategy is described as follows:

The DNA sequence encoding for Ck,-10, ATTC. # 75849, was constructed by PCR on the original EST cloned using two primers: the 5' primer 5' GGAAAGCTTATGAAAGTTTCTGCAGTGC 3' (SEQ ID NO:11) contains a HindIII site followed by 19 nucleotides of Ckβ-10 coding sequence starting from the initiation codon; the 3' sequence 5' CGCTCTAGATCAAGCGTAGTCTGG-GACGTCGTATGGGTAAG TCTTCAGGGTGTGAGCT 3' (SEQ ID NO:12) contains complementary sequences to XbaI site, translation stop codon, HA tag and the last 19 nucleotides of the Ckβ-10 coding sequence (not including the stop codon). Therefore, the PCR product contains a HindIII site, Ckβ-10 coding sequence followed by HA tag fused in frame, a translation termination stop codon next to the HA tag, and an XbaI site. The PCR amplified DNA fragment and the vector, pcDNAI/Amp, were digested with HindIII and BamH1 restriction enzyme and ligated. The ligation mixture was transformed into *E. coli* strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant Ckβ-10, COS cells were transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the Ckβ-10 HA protein was detected by radiolabelling and immunoprecipitation method. (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media were precipitated with a HA specific monoclonal antibody. Proteins precipitated were analyzed by SDS-PAGE.

EXAMPLE 5

Cloning and Expression of Ckβ-10 Using the Baculovirus Expression System

The DNA sequence encoding the full length Ckβ-10 protein, ATCC # 75849, was amplified using PCR oligonucleotide primers.

This expression vector contains the strong polyhedrin corresponding to the 5' and 3' sequences of the gene.

The 5' primer has the sequence 5' CGCGGGATCCT TAACCTTCAACATGAAA (SEQ ID NO:13) and contains a BamHI restriction enzyme site (in bold) followed by 12 nucleotides resembling an efficient signal for the initiation of translation in eukaryotic cells (J. Mol. Biol. 1987, 196, 947–950, Kozak, M.), and just behind, is the first 6 nucleotides of the Ckβ-10 coding sequence (the initiation codon for translation "ATG" is underlined).

The 3' primer has the sequence 5' CGCGGGTACC TTAACACATAGTACATTTT (SEQ ID NO:14) and contains the cleavage site for the restriction endonuclease Asp781 and 19 nucleotides complementary to the 3' non-translated sequence of the Ckβ-10 gene. The amplified sequences were isolated from a 1% agarose gel using a commercially available kit ("GENECLEAN®," BIO 101 Inc., La Jolla, Calif.). The fragment was then digested with the endonucleases BamHI and Asp781 and then purified again on a 1% agarose gel. This fragment is designated F2.

The vector pRG1 (modification of pVL941 vector, discussed below) is used for the expression of the Ckβ-10 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases BamHI and Asp781. The polyadenylation site of the simian virus (SV)40 is used for efficient polyadenylation. For an easy selection of recombinant viruses the beta-galactosidase gene from *E.coli* is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid was digested with the restriction enzymes BamH1 and Asp781 and then dephosphorylated using calf intestinal phosphatase by procedures known in the art. The DNA was then isolated from a 1% agarose gel. This vector DNA is designated V2.

Fragment F2 and the dephosphorylated plasmid V2 were ligated with T4 DNA ligase. *E.coli* HB101 cells were then transformed and bacteria identified that contained the plasmid (pBacCkβ-10) with the Ckβ-10 gene using the enzymes BamHI and Asp781. The sequence of the cloned fragment was confirmed by DNA sequencing.

5 μg of the plasmid pBacCkβ-10 were cotransfected with 1.0 μg of a commercially available linearized baculovirus ("BACULOGOLD® baculovirus DNA", Pharmingen, San Diego, Calif.) using the lipofection method (Felgner et al. Proc. Natl. Acad. Sci. USA, 84:7413–7417 (1987)).

1 μg of BACULOGOLD® virus DNA and 5 μg of the plasmid pBacCkβ-10 were mixed in a sterile well of a microtiter plate containing 50 μl of serum free Grace's medium (Life Technologies Inc., Gaithersburg, Md.). Afterwards 10 μl LIPOFECTIN® plus 90 μl Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution of the viruses was added to the cells, blue stained plaques were picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculoviruses was used to infect Sf9 cells seeded in 35 mm dishes. Four days later the supernatants of these culture dishes were harvested and then stored at 4 EC.

Sf9 cells were grown in Grace's medium supplemented with 10% heat-inactivated FBS. The cells were infected with the recombinant baculovirus V-Ckβ-10 at a multiplicity of infection (MOI) of 2. Six hours later the medium was removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) were added. The cells were further incubated for 16 hours before they were harvested by centrifugation and the labelled proteins visualized by SDS-PAGE and autoradiography.

EXAMPLE 6

Expression Via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turn upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindHIII and subsequently treated with calf intestinal phosphatase. The linear vector is fractionated on agarose gel and purified using glass beads.

The cDNA encoding a polypeptide of the present invention is amplified using PCR primers which correspond to 5' and 3' end sequences respectably. The 5' primer containing an EcoRI site and the 3' primer further includes a HindIII site. Equal quantities of the Moloney murine sarcoma virus linear backbone and the amplified EcoRI and HindIII fragment are added together, in the presence of the T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells.

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

SEQUENCE LISTING

<160> NUMBER OF SEQ ID NOS: 14

<210> SEQ ID NO 1
<211> LENGTH: 291
<212> TYPE: DNA
<213> ORGANISM: Homo sapiens -continued

```
<220> FEATURE:
<221> NAME/KEY: CDS
<222> LOCATION: (1)..(288)
<223> OTHER INFORMATION:

<400> SEQUENCE: 1 atg tgc tgt acc aag agt ttg ctc ctg gct gct ttg atg tca gtg ctg      48
Met Cys Cys Thr Lys Ser Leu Leu Leu Ala Ala Leu Met Ser Val Leu
1               5                   10                  15 cta ctc cac ctc tgc ggc gaa tca gaa gca gca agc aac ttt gac tgc      96
Leu Leu His Leu Cys Gly Glu Ser Glu Ala Ala Ser Asn Phe Asp Cys
            20                  25                  30 tgt ctt gga tac aca gac cgt att ctt cat cct aaa ttt att gtg ggc     144
Cys Leu Gly Tyr Thr Asp Arg Ile Leu His Pro Lys Phe Ile Val Gly
        35                  40                  45 ttc aca cgg cag ctg gcc aat gaa ggc tgt gac atc aat gct atc atc     192
Phe Thr Arg Gln Leu Ala Asn Glu Gly Cys Asp Ile Asn Ala Ile Ile
    50                  55                  60 ttt cac aca aag aaa aag ttg tct gtg tgc gca aat cca aaa cag act     240
Phe His Thr Lys Lys Lys Leu Ser Val Cys Ala Asn Pro Lys Gln Thr
65                  70                  75                  80 tgg gtg aaa tat att gtg cgt ctc ctc agt aaa aaa gtc aag aac atg     288
Trp Val Lys Tyr Ile Val Arg Leu Leu Ser Lys Lys Val Lys Asn Met
                85                  90                  95 taa                                                                  291

<210> SEQ ID NO 2
<211> LENGTH: 96
<212> TYPE: PRT
<213> ORGANISM: Homo sapiens

<400> SEQUENCE: 2

Met Cys Cys Thr Lys Ser Leu Leu Leu Ala Ala Leu Met Ser Val Leu
1               5                   10                  15

Leu Leu His Leu Cys Gly Glu Ser Glu Ala Ala Ser Asn Phe Asp Cys
            20                  25                  30

Cys Leu Gly Tyr Thr Asp Arg Ile Leu His Pro Lys Phe Ile Val Gly
        35                  40                  45

Phe Thr Arg Gln Leu Ala Asn Glu Gly Cys Asp Ile Asn Ala Ile Ile
    50                  55                  60

Phe His Thr Lys Lys Lys Leu Ser Val Cys Ala Asn Pro Lys Gln Thr
65                  70                  75                  80

Trp Val Lys Tyr Ile Val Arg Leu Leu Ser Lys Lys Val Lys Asn Met
                85                  90                  95

<210> SEQ ID NO 3
<211> LENGTH: 297
<212> TYPE: DNA
<213> ORGANISM: Homo sapiens
<220> FEATURE:
<221> NAME/KEY: CDS
<222> LOCATION: (1)..(294)
<223> OTHER INFORMATION:

<400> SEQUENCE: 3 atg aaa gtt tct gca gtg ctt ctg tgc ctg ctg ctc atg aca gca gct      48
Met Lys Val Ser Ala Val Leu Leu Cys Leu Leu Leu Met Thr Ala Ala
1               5                   10                  15 ttc aac ccc cag gga ctt gct cag cca gat gca ctc aac gtc cca tct      96
Phe Asn Pro Gln Gly Leu Ala Gln Pro Asp Ala Leu Asn Val Pro Ser
            20                  25                  30
```

```
act tgc tgc ttc aca ttt agc agt aag aag atc tcc ttg cag agg ctg      144
Thr Cys Cys Phe Thr Phe Ser Ser Lys Lys Ile Ser Leu Gln Arg Leu
         35                  40                  45 aag agc tat gtg atc acc acc agc agg tgt ccc cag aag gct gtc atc      192
Lys Ser Tyr Val Ile Thr Thr Ser Arg Cys Pro Gln Lys Ala Val Ile
 50                  55                  60 ttc aga acc aaa ctg ggc aag gag atc tgt gct gac cca aag gag aag      240
Phe Arg Thr Lys Leu Gly Lys Glu Ile Cys Ala Asp Pro Lys Glu Lys
 65                  70                  75                  80 tgg gtc cag aat tat atg aaa cac ctg ggc cgg aaa gct cac acc ctg      288
Trp Val Gln Asn Tyr Met Lys His Leu Gly Arg Lys Ala His Thr Leu
                 85                  90                  95 aag act tga                                                          297
Lys Thr <210> SEQ ID NO 4
<211> LENGTH: 98
<212> TYPE: PRT
<213> ORGANISM: Homo sapiens

<400> SEQUENCE: 4

Met Lys Val Ser Ala Val Leu Leu Cys Leu Leu Leu Met Thr Ala Ala
 1               5                  10                  15

Phe Asn Pro Gln Gly Leu Ala Gln Pro Asp Ala Leu Asn Val Pro Ser
                 20                  25                  30

Thr Cys Cys Phe Thr Phe Ser Ser Lys Lys Ile Ser Leu Gln Arg Leu
         35                  40                  45

Lys Ser Tyr Val Ile Thr Thr Ser Arg Cys Pro Gln Lys Ala Val Ile
 50                  55                  60

Phe Arg Thr Lys Leu Gly Lys Glu Ile Cys Ala Asp Pro Lys Glu Lys
 65                  70                  75                  80

Trp Val Gln Asn Tyr Met Lys His Leu Gly Arg Lys Ala His Thr Leu
                 85                  90                  95

Lys Thr

<210> SEQ ID NO 5
<211> LENGTH: 26
<212> TYPE: DNA
<213> ORGANISM: Artificial sequence
<220> FEATURE:
<223> OTHER INFORMATION: Contains a SphI restriction enzyme site
      followed by 17 nucleotides of Ckbeta-4 coding sequence.

<400> SEQUENCE: 5
cccgcatgca agcagcaagc aacttt                                          26

<210> SEQ ID NO 6
<211> LENGTH: 30
<212> TYPE: DNA
<213> ORGANISM: Artificial sequence
<220> FEATURE:
<223> OTHER INFORMATION: Contains complementary sequences to a BamH1
      site and is followed by 21 nucleotides of gene specific sequences
      preceding the termination codon.

<400> SEQUENCE: 6
aaaggatccc atgttcttga cttttttact                                      30

<210> SEQ ID NO 7
<211> LENGTH: 27
<212> TYPE: DNA
<213> ORGANISM: Artificial sequence
```

```
-continued

<220> FEATURE:
<223> OTHER INFORMATION: Contains a SphI restriction enzyme site
      followed by 19 nucleotides of Ckbeta-10 coding sequence.

<400> SEQUENCE: 7
cccgcatgca gccagatgca ctcaacg                                       27

<210> SEQ ID NO 8
<211> LENGTH: 28
<212> TYPE: DNA
<213> ORGANISM: Artificial sequence
<220> FEATURE:
<223> OTHER INFORMATION: Contains complementary sequences to a BamH1
      site and is followed by 19 nucleotides of gene specific sequences
      preceding the termination codon.

<400> SEQUENCE: 8
aaaggatcca gtcttcaggg tgtgagct                                      28

<210> SEQ ID NO 9
<211> LENGTH: 29
<212> TYPE: DNA
<213> ORGANISM: Artificial sequence
<220> FEATURE:
<223> OTHER INFORMATION: Contains a HindIII site followed by 20
      nucleotides of Ckbeta-4 coding sequence starting from the
      initiation codon

<400> SEQUENCE: 9
ggaaagctta tgtgctgtac caagagttt                                     29

<210> SEQ ID NO 10
<211> LENGTH: 59
<212> TYPE: DNA
<213> ORGANISM: Artificial sequence
<220> FEATURE:
<223> OTHER INFORMATION: Contains complementary sequences to XbaI site,
      translation stop codon, HA tag and the last 20 nucleotides of the
      Ckbeta-4 coding sequence

<400> SEQUENCE: 10
cgctctagat taagcgtagt ctgggacgtc gtatgggtaa catggttcct tgacttttt    59

<210> SEQ ID NO 11
<211> LENGTH: 28
<212> TYPE: DNA
<213> ORGANISM: Artificial sequence
<220> FEATURE:
<223> OTHER INFORMATION: Contains a HindIII site followed by 19
      nucleotides of Ckbeta-10 coding sequence starting from the
      initiation codon.

<400> SEQUENCE: 11
ggaaagctta tgaaagtttc tgcagtgc                                      28

<210> SEQ ID NO 12
<211> LENGTH: 58
<212> TYPE: DNA
<213> ORGANISM: Artificial sequence
<220> FEATURE:
<223> OTHER INFORMATION: Contains complementary sequences to XbaI site,
      translation stop codon, HA tag and the last 19 nucleotides of the
      Ckbeta-10 coding sequence.

<400> SEQUENCE: 12
cgctctagat caagcgtagt ctgggacgtc gtatgggtaa gtcttcaggg tgtgagct     58
```

-continued

```
<210> SEQ ID NO 13
<211> LENGTH: 28
<212> TYPE: DNA
<213> ORGANISM: Artificial sequence
<220> FEATURE:
<223> OTHER INFORMATION: Contains a BamHI restriction enzyme site
      followed by 12 nucleotides resembling an efficient signal for the
      initiation of translation in eukaryotic cells.

<400> SEQUENCE: 13
cgcgggatcc ttaaccttca acatgaaa                                          28

<210> SEQ ID NO 14
<211> LENGTH: 29
<212> TYPE: DNA
<213> ORGANISM: Artificial sequence
<220> FEATURE:
<223> OTHER INFORMATION: Contains the cleavage site for the restriction
      endonuclease Asp781 and 19 nucleotides complementary to the 3'
      non-translated sequence of the Ckbeta-10 gene.

<400> SEQUENCE: 14
cgcgggtacc ttaacacata gtacatttt                                         29
```

What is claimed is:

1. An isolated nucleic acid molecule comprising a polynucleotide selected from the group consisting of:
   (a) a polynucleotide encoding amino acid residues 24 to 98 of SEQ ID NO: 4; and
   (b) a polynucleotide encoding amino acid residues 1 to 98 of SEQ ID NO: 4.

2. The isolated nucleic acid molecule of claim 1, wherein said polynucleotide is (a).

3. The isolated nucleic acid molecule of claim 1, wherein said polynucleotide is (b).

4. A vector comprising the isolated nucleic acid molecule of claim 1.

5. The vector of claim 4 wherein the nucleic acid molecule is operably associated with a heterologous regulatory sequence that controls gene expression.

6. An isolated recombinant host cell comprising the isolated nucleic acid molecule of claim 1.

7. The isolated recombinant host cell of claim 6 wherein the nucleic acid molecule is operably associated with a heterologous regulatory sequence that controls gene expression.

8. A method for producing a polypeptide, comprising: (a) culturing the isolated recombinant host cell of claim 6 under conditions suitable to produce the polypeptide encoded by said polynucleotide; and recovering the polypeptide from the cell culture.

* * * * *

UNITED STATES PATENT AND TRADEMARK OFFICE
CERTIFICATE OF CORRECTION

| | | |
|---|---|---|
| PATENT NO. | : 7,183,081 B2 | |
| APPLICATION NO. | : 10/893995 | |
| DATED | : February 27, 2007 | |
| INVENTOR(S) | : Li et al. | |

It is certified that error appears in the above-identified patent and that said Letters Patent is hereby corrected as shown below:

Title page at item (56) References Cited, Other Publications (continued):

On page 2, column 2, in the Lerner, Richard A. reference, delete "repertorie" and replace with --repertoire--.

On page 2, column 2, in the Nakao et al. reference, delete "*Molec. Cell. Ciol.*" and replace with --*Molec. Cell. Biol.*--.

On page 2, column 2, in the Opdennaker et al. reference, delete "of he cDNA" and replace with --of the cDNA-- and delete "191(2)535-542" and replace with --191(2):535-542--.

On page 3, column 1, in the Hoover et al. reference, delete "277940):37647-37654" and replace with --277(40):37647-37654--.

On page 3, column 1, in the Matsui et al. reference, delete "Seelctive" and replace with --Selective--.

On page 3, column 2, in the Akahoshi et al. reference, delete "(CCL190 by" and replace with --(CCL19) BY--.

In the Drawings:
Replace Sheet 3 of 3 with the accompanying Sheet 3 of 3.

At column 1, line 8, delete "(now U.S. Pat. No. 6,921,645), issued Jul. 26, 2005," and replace with --(now U.S. Pat. No. 6,921,645, issued Jul. 26, 2005),--.

At column 23, line 11 of the patent, delete "at 27° C. for four" and replace with -- at 27° C for four--.

UNITED STATES PATENT AND TRADEMARK OFFICE
CERTIFICATE OF CORRECTION

| | | |
|---|---|---|
| PATENT NO. | : 7,183,081 B2 | |
| APPLICATION NO. | : 10/893995 | |
| DATED | : February 27, 2007 | |
| INVENTOR(S) | : Li et al. | |

It is certified that error appears in the above-identified patent and that said Letters Patent is hereby corrected as shown below:

In the Sequence Listing:

Replace the Sequence Listing with the accompanying Sequence Listing.

25 EAASNFDCCLGYTDRILHPKFIVGFTRQLANEGCDINAIIFHTKKLSVC 74
     ..:  .  .||.  |:  .  :  .  .::::.|.  .||:..:.:|
 1 HPGIPSACCFRVTNICKISFQALKSYKIITSSKCPQTAIVFEIKPDKMIC 50

75 ANPKQTWVKYIVRLLSKKVK 94
   |:|.  .||:.  ||.  .:|...
51 ADPRXXWVQDAKKYLDQISQ 70

FIG. 3

1 MKVSAVLLCLLLMTAAFNPQGLAQPDALNVPSTCCFTFSSKKISLQRLKS 50
   ||.|.|||||.||.|||||||  ::|..:||||||  |  .||.|||.|
 1 MKASAALLCLLLTAAAFSPQGLAQPVGINTSTTCCYRFINKKIPKQRLES 50

51 YVITT.SRCPQKAVIFRTKLGKEICADPKEKWVQNYMKHLGRKAHTLKT 98
   |.||.  |:|:.|||||||||.|:||||||:|||||  .:|||||.:|.:|
51 YRRTTSSHCPREAVIFKTKLDKEICADPTQKWVQDFMKHLDKKTQTPKL 99

FIG. 4

UNITED STATES PATENT AND TRADEMARK OFFICE
CERTIFICATE OF CORRECTION

PATENT NO. : 7,183,081 B2
APPLICATION NO. : 10/893995
DATED : February 27, 2007
INVENTOR(S) : Li et al.

It is certified that error appears in the above-identified patent and that said Letters Patent is hereby corrected as shown below:

Delete sequences listing beginning at column 23 and 24 ending at column 31 and 32 and substitute therefor the attached sequences listing as shown on the attached pages.

SEQUENCE LISTING

```
<110>  Li et al.

<120>  Human CkB-10 Polynucleotides

<130>  PF132P1D3

<140>  US 10/893,995
<141>  2004-07-20

<150>  US 10/164,621
<151>  2002-06-10

<150>  US 09/261,201
<151>  1999-03-03

<150>  US 08/458,355
<151>  1995-06-02

<150>  PCT/US94/09484
<151>  1994-08-23

<160>  16

<170>  PatentIn version 3.3

<210>  1
<211>  291
<212>  DNA
<213>  Homo sapiens

<220>
<221>  CDS
<222>  (1)..(288)

<400>  1
atg tgc tgt acc aag agt ttg ctc ctg gct gct ttg atg tca gtg ctg
Met Cys Cys Thr Lys Ser Leu Leu Leu Ala Ala Leu Met Ser Val Leu
1               5                   10                  15 cta ctc cac ctc tgc ggc gaa tca gaa gca gca agc aac ttt gac tgc
Leu Leu His Leu Cys Gly Glu Ser Glu Ala Ala Ser Asn Phe Asp Cys
                20                  25                  30 tgt ctt gga tac aca gac cgt att ctt cat cct aaa ttt att gtg ggc
Cys Leu Gly Tyr Thr Asp Arg Ile Leu His Pro Lys Phe Ile Val Gly
            35                  40                  45 ttc aca cgg cag ctg gcc aat gaa ggc tgt gac atc aat gct atc atc
Phe Thr Arg Gln Leu Ala Asn Glu Gly Cys Asp Ile Asn Ala Ile Ile
        50                  55                  60 ttt cac aca aag aaa aag ttg tct gtg tgc gca aat cca aaa cag act
Phe His Thr Lys Lys Lys Leu Ser Val Cys Ala Asn Pro Lys Gln Thr
65                  70                  75                  80 tgg gtg aaa tat att gtg cgt ctc ctc agt aaa aaa gtc aag aac atg
Trp Val Lys Tyr Ile Val Arg Leu Leu Ser Lys Lys Val Lys Asn Met
                85                  90                  95
```

UNITED STATES PATENT AND TRADEMARK OFFICE
CERTIFICATE OF CORRECTION

PATENT NO.       : 7,183,081 B2                                             Page 5 of 9
APPLICATION NO.  : 10/893995
DATED            : February 27, 2007
INVENTOR(S)      : Li et al.

It is certified that error appears in the above-identified patent and that said Letters Patent is hereby corrected as shown below:

```
taa                                                                 291

<210>  2
<211>  96
<212>  PRT
<213>  Homo sapiens

<400>  2

Met Cys Cys Thr Lys Ser Leu Leu Ala Ala Leu Met Ser Val Leu
1               5                  10                 15

Leu Leu His Leu Cys Gly Glu Ser Glu Ala Ala Ser Asn Phe Asp Cys
            20                  25                  30

Cys Leu Gly Tyr Thr Asp Arg Ile Leu His Pro Lys Phe Ile Val Gly
            35                  40                  45

Phe Thr Arg Gln Leu Ala Asn Glu Gly Cys Asp Ile Asn Ala Ile Ile
        50                  55                  60

Phe His Thr Lys Lys Lys Leu Ser Val Cys Ala Asn Pro Lys Gln Thr
65                  70                  75                  80

Trp Val Lys Tyr Ile Val Arg Leu Leu Ser Lys Lys Val Lys Asn Met
                    85                  90                  95

<210>  3
<211>  297
<212>  DNA
<213>  Homo sapiens

<220>
<221>  CDS
<222>  (1)..(294)

<400>  3
atg aaa gtt tct gca gtg ctt ctg tgc ctg ctg ctc atg aca gca gct      48
Met Lys Val Ser Ala Val Leu Leu Cys Leu Leu Leu Met Thr Ala Ala
1               5                  10                 15 ttc aac ccc cag gga ctt gct cag cca gat gca ctc aac gtc cca tct      96
Phe Asn Pro Gln Gly Leu Ala Gln Pro Asp Ala Leu Asn Val Pro Ser
            20                  25                  30 act tgc tgc ttc aca ttt agc agt aag aag atc tcc ttg cag agg ctg     144
Thr Cys Cys Phe Thr Phe Ser Ser Lys Lys Ile Ser Leu Gln Arg Leu
            35                  40                  45 aag agc tat gtg atc acc acc agc agg tgt ccc cag aag gct gtc atc     192
Lys Ser Tyr Val Ile Thr Thr Ser Arg Cys Pro Gln Lys Ala Val Ile
        50                  55                  60
```

UNITED STATES PATENT AND TRADEMARK OFFICE
CERTIFICATE OF CORRECTION

PATENT NO.       : 7,183,081 B2
APPLICATION NO.  : 10/893995
DATED            : February 27, 2007
INVENTOR(S)      : Li et al.

It is certified that error appears in the above-identified patent and that said Letters Patent is hereby corrected as shown below:

```
ttc aga acc aaa ctg ggc aag gag atc tgt gct gac cca aag gag aag      240
Phe Arg Thr Lys Leu Gly Lys Glu Ile Cys Ala Asp Pro Lys Glu Lys
65                  70                  75                  80 tgg gtc cag aat tat atg aaa cac ctg ggc cgg aaa gct cac acc ctg      288
Trp Val Gln Asn Tyr Met Lys His Leu Gly Arg Lys Ala His Thr Leu
                85                  90                  95 aag act tga                                                          297
Lys Thr <210>  4
<211>  98
<212>  PRT
<213>  Homo sapiens

<400>  4

Met Lys Val Ser Ala Val Leu Leu Cys Leu Leu Met Thr Ala Ala
1               5                   10                  15

Phe Asn Pro Gln Gly Leu Ala Gln Pro Asp Ala Leu Asn Val Pro Ser
                20                  25                  30

Thr Cys Cys Phe Thr Phe Ser Ser Lys Lys Ile Ser Leu Gln Arg Leu
        35                  40                  45

Lys Ser Tyr Val Ile Thr Thr Ser Arg Cys Pro Gln Lys Ala Val Ile
        50                  55                  60

Phe Arg Thr Lys Leu Gly Lys Glu Ile Cys Ala Asp Pro Lys Glu Lys
65                  70                  75                  80

Trp Val Gln Asn Tyr Met Lys His Leu Gly Arg Lys Ala His Thr Leu
                85                  90                  95

Lys Thr

<210>  5
<211>  26
<212>  DNA
<213>  Artificial sequence

<220>
<223>  Contains a SphI restriction enzyme site followed by 17 nucleotides of Ckbet <400>  5
cccgcatgca agcagcaagc aacttt                                          26
```

Page 6 of 9

UNITED STATES PATENT AND TRADEMARK OFFICE
CERTIFICATE OF CORRECTION

PATENT NO. : 7,183,081 B2
APPLICATION NO. : 10/893995
DATED : February 27, 2007
INVENTOR(S) : Li et al.

It is certified that error appears in the above-identified patent and that said Letters Patent is hereby corrected as shown below:

```
<210>  6
<211>  30
<212>  DNA
<213>  Artificial sequence

<220>
<223>  Contains complementary sequences to a BamHI site and is followed by 21 nucl <400>  6
aaaggatccc atgttcttga cttttttact                                      30

<210>  7
<211>  27
<212>  DNA
<213>  Artificial sequence

<220>
<223>  Contains a SphI restriction enzyme site followed by 19 nucleotides of Ckbet <400>  7
cccgcatgca gccagatgca ctcaacg                                         27

<210>  8
<211>  28
<212>  DNA
<213>  Artificial sequence

<220>
<223>  Contains complementary sequences to a BamHI site and is followed by 19 nucl <400>  8
aaaggatcca gtcttcaggg tgtgagct                                        28

<210>  9
<211>  29
<212>  DNA
<213>  Artificial sequence

<220>
<223>  Contains a HindIII site followed by 20 nucleotides of Ckbeta-4 coding seque <400>  9
ggaaagctta tgtgctgtac caagagttt                                       29

<210>  10
<211>  59
<212>  DNA
<213>  Artificial sequence

<220>
<223>  Contains complementary sequences to XbaI site, translation stop codon, HA t <400>  10
cgctctagat taagcgtagt ctgggacgtc gtatgggtaa catggttcct tgactttt       59
```

UNITED STATES PATENT AND TRADEMARK OFFICE
CERTIFICATE OF CORRECTION

PATENT NO. : 7,183,081 B2  Page 8 of 9
APPLICATION NO. : 10/893995
DATED : February 27, 2007
INVENTOR(S) : Li et al.

It is certified that error appears in the above-identified patent and that said Letters Patent is hereby corrected as shown below:

```
<210> 11
<211> 28
<212> DNA
<213> Artificial sequence

<220>
<223> Contains a HindIII site followed by 19 nucleotides of Ckbeta-10 coding seq
<400> 11
ggaaagctta tgaaagtttc tgcagtgc                                       28

<210> 12
<211> 58
<212> DNA
<213> Artificial sequence

<220>
<223> Contains complementary sequences to XbaI site, translation stop codon, HA t
<400> 12
cgctctagat caagcgtagt ctgggacgtc gtatgggtaa gtcttcaggg tgtgagct      58

<210> 13
<211> 28
<212> DNA
<213> Artificial sequence

<220>
<223> Contains a BamHI restriction enzyme site followed by 12 nucleotides resembl
<400> 13
cgcgggatcc ttaaccttca acatgaaa                                       28

<210> 14
<211> 29
<212> DNA
<213> Artificial sequence

<220>
<223> Contains the cleavage site for the restriction endonuclease Asp781 and 19 n
<400> 14
cgcgggtacc ttaacacata gtacatttt                                      29

<210> 15
<211> 70
<212> PRT
<213> Homo sapiens

<220>
<221> misc_feature
<222> (55)..(56)
<223> Xaa can be any naturally occurring amino acid.

<400> 15
```

UNITED STATES PATENT AND TRADEMARK OFFICE
CERTIFICATE OF CORRECTION

PATENT NO.         : 7,183,081 B2
APPLICATION NO.    : 10/893995
DATED              : February 27, 2007
INVENTOR(S)        : Li et al.

It is certified that error appears in the above-identified patent and that said Letters Patent is hereby corrected as shown below:

```
His Pro Gly Ile Pro Ser Ala Cys Cys Phe Arg Val Thr Asn Ile Cys
1            5                   10                  15

Lys Ile Ser Phe Gln Ala Leu Lys Ser Tyr Lys Ile Ile Thr Ser Ser
                20              25              30

Lys Cys Pro Gln Thr Ala Ile Val Phe Glu Ile Lys Pro Asp Lys Met
            35              40              45

Ile Cys Ala Asp Pro Arg Xaa Xaa Trp Val Gln Asp Ala Lys Lys Tyr
    50              55              60

Leu Asp Gln Ile Ser Gln
65              70

<210> 16
<211> 99
<212> PRT
<213> Homo sapiens

<400> 16

Met Lys Ala Ser Ala Ala Leu Leu Cys Leu Leu Leu Thr Ala Ala Ala
1            5                   10                  15

Phe Ser Pro Gln Gly Leu Ala Gln Pro Val Gly Ile Asn Thr Ser Thr
                20              25              30

Thr Cys Cys Tyr Arg Phe Ile Asn Lys Lys Ile Pro Lys Gln Arg Leu
            35              40              45

Glu Ser Tyr Arg Arg Thr Thr Ser Ser His Cys Pro Arg Glu Ala Val
    50              55              60

Ile Phe Lys Thr Lys Leu Asp Lys Glu Ile Cys Ala Asp Pro Thr Gln
65              70              75              80

Lys Trp Val Gln Asp Phe Met Lys His Leu Asp Lys Lys Thr Gln Thr
                85              90              95

Pro Lys Leu
```

Signed and Sealed this

Twenty-first Day of August, 2007

JON W. DUDAS
*Director of the United States Patent and Trademark Office*